United States Patent [19]

Cotter et al.

[11] Patent Number: 5,411,894
[45] Date of Patent: May 2, 1995

[54] METHOD OF USING TISSUE AND CELL ADHESIVE PREPARATIONS FOR BIOLOGICAL TEST SYSTEMS

[75] Inventors: Darlene L. Cotter, Fox Lake; Barbara L. Abry, Mundelein; Ray A. Weigand, Libertyville, all of Ill.

[73] Assignee: Abbott Laboratories, Abbott Park, Ill.

[21] Appl. No.: 496,463

[22] Filed: Mar. 20, 1990

[51] Int. Cl.$^6$ .............. G01N 1/30; G02B 21/34
[52] U.S. Cl. .............. 436/174; 436/176; 436/166; 422/57
[58] Field of Search .............. 436/8–18, 436/174, 518, 524, 527, 528, 531, 15, 17–18, 174, 176, 177, 166; 424/3; 422/55, 57, 69, 73

[56] References Cited

U.S. PATENT DOCUMENTS

| | | | |
|---|---|---|---|
| 3,959,080 | 5/1976 | Orth et al. | 436/530 X |
| 4,379,847 | 4/1983 | Fruitstone et al. | 436/17 X |
| 4,436,825 | 3/1984 | Lalezari | 436/520 |
| 4,493,821 | 1/1985 | Harrison | 436/18 X |
| 4,756,884 | 7/1988 | Hillman et al. | 422/73 |
| 4,774,058 | 9/1988 | Mehl | 422/101 |
| 4,812,401 | 3/1989 | Tarnowski et al. | 436/520 |
| 4,839,231 | 6/1989 | Vandekerchkove | 428/441 |
| 4,868,106 | 9/1989 | Ito et al. | 422/56 X |
| 4,960,691 | 10/1990 | Gordon et al. | 422/56 X |
| 4,992,383 | 2/1991 | Farnsworth | 436/178 X |

OTHER PUBLICATIONS

Hackett, C. J. et al., "A convenient culture chamber for observation and embedding of macrophage monolayers for transmission electron microscopy", Journal of Microscopy, vol. 126, pp. 207–210 (1982).

Cuevas, J. H. et al., IRCS Medical Science, vol. 11, pp. 30–31 (1983).

*Primary Examiner*—Jeffrey R. Snay
*Attorney, Agent, or Firm*—Lawrence S. Pope

[57] ABSTRACT

The present invention includes adhesive solutions, devices and a method for the preparation of histological, cytological, immunological and proteinaceous samples for evaluation. The devices involve at least one sample deposition area formed from an adhesive composition, containing from about 0.003% to about 1.0% 1,5-dimethyl-1,5-diazaundecamethylene polymethobromide in a suitable solvent, wherein the adhesive composition is dried upon a solid support material such as a glass microscope slide or the like.

2 Claims, No Drawings

METHOD OF USING TISSUE AND CELL ADHESIVE PREPARATIONS FOR BIOLOGICAL TEST SYSTEMS

BACKGROUND OF THE INVENTION

1. Field of the Invention

The present invention relates to an adhesive solution and method for the preparation of histological, cytological, immunological and proteinaceous test and control samples for evaluation, as well as to novel slides and test systems made possible by the unique properties of the adhesive solution. In particular, the invention relates to the use of a 1,5-dimethyl-1,5-diazaundecamethylene polymethobromide (hexadimethrine bromide) composition as a tissue adhesive for tissue sections, whole cells and fine-needle aspirates.

2. Description of Related Art

The use of quaternary ammonium polymers to aid in the attachment of cell preparations to the solid surface of a culture dish or membrane is known. Generally, compositions containing a polycationic substance together with protein materials are used as a mixture to promote cell adhesion to the culture vessel. In addition, solutions containing the polycation are typically applied directly to the tissue or cell sample. Hackett et al., in Journal of Microscopy, 126, 207-210 (1982), describe a method of treating a dialysis membrane with a mixture of hexadimethrine bromide and normal mouse serum to prepare a cell culture chamber. The hexadimethrine bromide serves to adhere the protein in the normal mouse serum to the dialysis membrane, but is not in itself responsible for the adherence of the cells to the solid support.

In IRCS Medical Science, 11, 30-31 (1983), Cuevas et al. disclose the use of poly-1-lysine or hexadimethrine bromide in culture vessels containing mammalian cells and growth medium. The polycations were found to improve glycolysis, cell adhesion and cell growth. According to the disclosure, up to five hours were allowed for cell attachment to the vessel before the polycation composition is added to the medium.

Other works of interest describe sample embedding techniques and materials, or complex preservative compositions, for the preparation of tissue and cell samples for evaluation. Healy et al. in U.S. Pat. No. 4,816,410 describe the use of an embedding medium, having a low temperature melting point, to enclose the sample upon the solid support. Harrison, J. in U.S. Pat. No. 4,493,381 describes a four component mixture of pyrrolid-2-one, a polyol, at least one urea and a zinc salt of a non-oxidizing organic or inorganic acid for use in preserving and fixing tissue or cell samples.

SUMMARY OF THE INVENTION

The present invention provides compositions and methods for producing devices suitable for the observation of tissue and cell samples. The adhesive compositions include a suitable solvent containing from about 0.003% (w/v) to about 1.0% (w/v) hexadimethrine bromide for the adhesion of a sample to a solid support material. The composition contains from about 0.003% (w/v) to about 0.06% (w/v) hexadimethrine bromide in preferred embodiments, and the solvent is distilled or deionized water. Optionally, the composition contains hexadimethrine bromide at a concentration of about 0.01% (w/v), and the composition can further include a protein stabilizer and/or an antimicrobial agent.

The present invention further provides devices for observing histological, cytological and proteinaceous samples, wherein at least one sample deposition area is formed by applying and drying the adhesive composition upon a solid support material. Typically, the solid support material is non-absorbent to and insoluble in water and can be selected from materials such as glass, polymethylacrylate, polystyrene, polyacrylamide, polyethylene, polypropylene, polycarbonates, polyvinylchloride and the like. Optionally, the deposition area may contain a blocking agent to prevent the nonspecific binding of subsequent reagents to the deposition area.

Histological, cytological and proteinaceous samples are prepared for observation by applying the sample to a solid support material having at least one substantially dry sample deposition area formed from an adhesive composition of the present invention and allowing the sample to adhere to the solid support.

DETAILED DESCRIPTION OF THE INVENTION

The present invention is a departure from the related art in that the invention provides an adhesive composition which is applied directly to a solid support material, such as a microscope slide or other test surface, and presents a substantially dry, non-fluid surface to which the sample is applied. Contact between the pretreated solid support and the sample results in the adhesion of the sample to the test surface such that only the act of placing the sample on the surface is required. The sample need not be disturbed by the use of embedding techniques or reagents, or preservative compositions.

The basic composition of the present invention employs hexadimethrine bromide (Polybrene®, Sigma, St. Louis, Mo.) as the adhesive component in a suitable solvent such as distilled water or deionized water. The concentration of hexadimethrine bromide in the adhesive solution can vary within a broad range of about 0.003% (w/v) to 1.0% (w/v). Generally, the hexadimethrine bromide concentration will be about 0.003% (w/v) to about 0.06% (w/v). In immunocytochemical assays of test samples suspected of containing progesterone receptor or estrogen receptor analyte, or of control samples known to contain progesterone receptor or estrogen receptor analyte, a 0.01% (w/v) hexadimethrine bromide composition has been found most suitable for use as an adhesive solution. The most appropriate percentage of hexadimethrine bromide in the adhesive composition may vary with any given sample to be studied, but the optimal concentration for use with a particular sample can be readily determined, without undue experimentation, as described in the examples which follow.

The novel adhesive composition of the present invention provides several advantages over known slide preparation reagents and methods. The hexadimethrine bromide adhesive solution unexpectedly demonstrated an increased adhesive capacity as compared to poly-amino acids such as poly-1-lysine, quaternary ammonium polymers such as Celquat® H-100 (polyquaternium-4; National Starch and Chemical Corporation, Bridgewater, N.J.), Celquat® L-200 (National Starch and Chemical Corporation) and Merquat® 100 (polyquaternium-6; Calgon Corporation, Rahway, N.J.) or other materials such as Copolymer 845 (GAF Corporation, New York, N.Y.). Furthermore, the precoated slides of the present invention can be provided to individual practitioners. Tissue sections or cell suspensions can then be directly applied by the user, and the slide can be immediately used for cell observation, or the slide and adhered material can be subjected to staining procedures or the addition of further reagents in the performance of a diagnostic assay. In addition, the precoated and dried slides of the present invention have an enhanced stability and can be stored for longer periods before use, as opposed to other adhesives such as poly-1-lysine with which only freshly coated slides are typically used. Moreover, the hexadimethrine bromide adhesive composition has no substantial effect upon the immunoreactivity of the sample, and therefore, the use of this composition decreases the risk of assay interference which may be caused by other sample preparation reagents.

Various other components can be present in the adhesive composition, and the presence or absence of such ingredients will depend upon the specific use. For example, in one embodiment of the present invention the adhesive composition can include an antimicrobial agent and/or a protein stabilizer.

One theory to explain the function of hexadimethrine bromide in the present invention is that the adhesive solution forms a dry film upon the solid support, which film has a charged surface to which the tissue, cell or protein material adheres. In contrast to other materials which were tested, such as poly-1-lysine, Celquat ® H-100, Celquat ® L-200, Merquat ® 100 and Copolymer 845, hexadimethrine bromide was unexpectedly found to provide an optimal combination of desired attributes which include enhanced adhesion of the sample to a pretreated solid support and the maintenance of both the cellular and immunological characteristics of the sample. Cell smears, simulating a fine-needle aspirate, have demonstrated a superior attachment to the solid support using hexadimethrine bromide.

The novel composition of the present invention is especially useful for the preparation of precoated solid supports to which the study sample of tissue sections (frozen, paraffin block, gelatin or other), whole cells, fine-needle aspirates or other proteinaceous material can be contacted. The composition is used as a solution to precoat slides or other solid support surfaces and thereby form at least one sample deposition area upon the surface of the solid support. The adhesive solution can be applied to a discrete or limited portion of the solid support to form the sample deposition area, but typically, the entire solid support, such as a microscope slide, is immersed in the adhesive solution and thereby coated. The adhesive solution typically remains upon the solid support for a period of about five to about sixty minutes. Alternatively, the solid support can be incubated with the adhesive solution overnight, i.e. approximately 18 hours. The solid support may then be rinsed in distilled or deionized water. The solid support is allowed to dry to result in a substantially dry precoated solid support. Such a precoated solid support can then be stored until needed or used immediately.

Suitable solid support materials are insoluble in water and are non-absorbent. Solid support materials include, but are not limited to, glass and plastic materials. Suitable plastics include polystyrene, polyacrylamide, polymethacrylate, polyethylene, polypropylene, polycarbonates, polyvinylchloride, nitrocellulose and the like.

The solid support devices made with the adhesive solution are readily used in preparing cell or tissue samples for direct observation, such as by means of a light microscope. The devices of the present invention are also advantageously used in diagnostic testing. A tissue, cell or protein sample can be contacted to the precoated device, whereby the sample adheres to the sample deposition area. Additional diagnostic assay reagents can then be contacted to the sample which adhered to the device.

In one embodiment of the present invention, the precoated device can be used for immunocytochemical staining of cellular proteins, such as estrogen receptors. A test sample suspected of containing the estrogen receptor analyte, or a control sample known to contain the analyte, is contacted to the solid support at the sample deposition area. The protein which adheres to the support may then be exposed to a fixative procedure which serves to stabilize the protein structure of the analyte such that the protein is less lablie and therefore does not readily undergo degradation which decreases the immunoreactivity of the adhered protein. The deposition area of the solid support may also optionally be treated with a protein blocking agent which prevents the nonspecific binding of subsequent reagents to the deposition area. An anti-estrogen receptor antibody can then be contacted to the deposition area thereby forming an antigen/antibody complex attached to the device. The antibody can be directly or indirectly labeled such that the resultant complex can be detected. With direct labeling, the anti-estrogen receptor antibody can be conjugated with a detectable label. Indirect labeling refers to the use of at least one additional assay reagent which is labeled and which can react with the adhered antigen/antibody complex thereby making the complex detectable.

The diagnostic assay devices of the present invention can be used with antigen/antibody specific binding members, as described above, or other members of specific binding pairs. The term "specific binding member", as used herein, refers to a member of a specific binding pair, i.e., two different molecules wherein one of the molecules specifically binds to the second molecule through chemical or physical means. In addition to antigen and antibody specific binding pair members, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example an analyte-analog or a specific binding member made by recombinant techniques. If the specific binding member is an immunoreactant it can be, for example, an antibody, antigen, hapten, or complex thereof, and if an antibody is used, it can be a monoclonal or polyclonal antibody, a recombinant protein or antibody, a mixture(s) or fragment(s) thereof, as well as a mixture of an antibody and other specific binding members. The details of the preparation of such antibodies and their suitability for use as specific binding members are well-known to those skilled-in-the-art.

The term "analyte", as used herein, refers to the material, compound or composition to be observed, detected or measured. "Analytes" include tissues, cells and proteinaceous materials which are either directly observed once adhered to the solid support or which have at least one epitope or binding site whereby additional reagents are complexed to enable the detection of the analyte upon the solid support.

"Conjugate", as used herein, refers to a substance comprising a detectable label covalently or non-covalently attached to a specific binding member or other substance which reacts with the analyte. The method of attachment is not critical to the present invention. The label enables the conjugate to produce a detectable signal that is directly or indirectly related to the amount of analyte in the test sample. The specific binding member component of the conjugate can be selected to directly bind to the analyte or to indirectly bind the analyte by means of an ancillary specific binding member, which is described in greater detail hereinafter.

The term "label", as used herein, typically refers to any substance which is capable of producing a signal that is detectable by visual or instrumental means. Various labels suitable for use in the present invention include labels which can produce signals through either chemical or physical means and can include enzymes and substrates; chromogens; catalysts; fluorescent compounds; chemiluminescent compounds; radioactive labels; direct visual labels including colloidal metallic particles such as gold, colloidal non-metallic particles such as selenium, dyed or colored particles such as a dyed plastic or a stained microorganism, organic polymer latex particles and liposomes or other vesicles containing directly visible substances; and the like. Labels also include the conventional dyes and stains such as methylene blue, creosol violet acetate, hematoxylin, and the like. as well as counterstains such as rosaniline, magenta II, picric acid and the like, and mitochondrial dyes such as actiflavin.

The selection of a particular label is not critical, but the label will be capable of generating a detectable signal either by itself, such as a visually detectable colored organic polymer latex particle or an instrumentally detectable fluorescent compound, or in conjunction with one or more additional signal producing components, such as an enzyme/substrate signal producing system. A variety of different conjugates can be formed by varying either the label or the specific binding member; it will be appreciated by one skilled-in-the-art that the choice involves consideration of the analyte to be detected and the desired means of detection.

"Signal producing component" refers to any substance capable of reacting with another assay reagent or with the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be reacted with the label to generate a detectable signal, e.g., when the label is an enzyme, amplification of the detectable signal is obtained by reacting the enzyme with one or more substrates or additional enzymes to produce a detectable reaction product.

An example of an enzyme/substrate signal producing system is the enzyme alkaline phosphatase, wherein the substrate used is nitro blue tetrazolium-5-bromo-4-chloro-3-indolyl phosphate or a derivative or analog thereof. In an alternative signal producing system, the label can be a fluorescent compound where no enzymatic manipulation of the label is required to produce the detectable signal. Fluorescent molecules such as fluorescein, phycobiliprotein, rhodamine and their derivatives and analogs are suitable for use as labels in such a system.

The term "ancillary specific binding member", as used herein, refers to any member of a specific binding pair which is used in the assay in addition to the specific binding members of the conjugate in forming a detectable complex upon the solid support. One or more ancillary specific binding members can be used in an assay. For example, an ancillary specific binding member can be capable of binding the conjugate to the analyte of interest, in instances where the analyte itself could not directly attach to the conjugate, or the ancillary specific binding member can be used to increase the amount of conjugate which can complex with the analyte in a binding reaction.

It will be appreciated by one skilled-in-the-art that the types of conjugates, solid support materials, and fixative reagents and blocking agents or procedures are not critical to the present invention which features the use of hexadimethrine bromide solutions as cell adhesives. Rather, such fixative reagents and blocking agents or procedures will be optimized dependent upon the analyte of interest, conjugate selection can be based upon ease of use and the desired means of detection (e.g., direct observation or detection via instrumentation) and the solid support can be selected based upon both the reagents used and their methods of use.

In an alternative embodiment of the present invention, the adhesive solution can be supplied to the user for the production of slides. The user incubates the solid support material with an adhesive solution containing from about 0.003% (w/v) to about 1.0% (w/v) of hexadimethrine bromide for approximately five minutes at room temperature, rinses the solid support and then allows the support to dry. The support is then ready for use or may be stored for approximately two months. Optionally, the adhesive solution contains from about 0.003% to about 0.06% of hexadimethrine bromide. Additionally, the solid support can be incubated with the composition for longer than five minutes and can be dried at temperatures greater than room temperature.

In yet another embodiment of the present invention, the novel adhesive solution can be used to precoat the solid support, such as a glass microscope slide, to which a tissue, cell or protein material is contacted and adhered thereby forming assay control slides. Such slides can include a sample deposition area for the application of a test sample suspected of containing the analyte of interest.

EXAMPLES

The following examples describe methods for producing the novel adhesive compositions and devices of the present invention, as well as assays which were performed in accordance with the present invention.

Example 1

Hexadimethrine Bromide Adhesive Solutions

Hexadimethrine bromide (1,5-dimethyl-1,5-diazaundecamethylene polymethobromide) was dissolved in distilled or deionized water to form adhesive solutions having final concentrations of about 0.003% (w/v) to about 1.0% (w/v). Glass microscope slides were immersed in the adhesive solutions for approximately five minutes. The slides were then rinsed two times in distilled or deionized water for approximately one minute per rinse. The slides were then air dried. The slides can be dried at room temperature or dried under heated conditions.

Example 2

Tissue Mounts

Tissue sections (approximately five microns thick) were cut in a cryostat and thaw mounted onto a hexadimethrine bromide precoated slide prepared substantially in accordance with the procedure described in Example 1. The slides were fixed by immersion in approximately 3.7% formaldehyde-phosphate buffered saline (PBS) for 10 to 15 minutes. The slides were then immersed in cold acetone at −10° to −25° C. for three to five minutes, immersed in cold acetone at −10° to −25° C. for one to three minutes and rinsed twice by immersion in room temperature PBS for four to six minutes per PBS bath. After the entire procedure was completed, the slides were stored in a specimen storage medium (PBS, 8.56% sucrose, 0.066% $MgCl_2 \cdot 6H_2O$, and 50% glycerol; or a substantially equivalent storage medium) for future use or were used in an immunocytochemistry assays such as an estrogen receptor immunocytochemical assay (Abbott ER-ICA Monoclonal; Abbott Laboratories, Abbott Park, Ill.), a progesterone receptor immunocytochemical assay (Abbott PgR-ICA Monoclonal; Abbott Laboratories, Abbott Park, Ill.) or other histological assay.

Tissue mount slides prepared from estrogen receptor-rich tissue and assayed with Abbott ER-ICA Monoclonal result in nuclei of estrogen receptor-rich cells being stained brown by the immunocytochemical reaction. Estrogen receptor-poor cell nuclei are stained blue/light-purple with a weak hematoxylin counterstain and lack the brown stain. The role of hexadimethrine bromide was to enhance attachment of the tissue section to the slide so that the tissue was retained on the slide during the fixation and staining process.

An exemplary immunocytochemical assay employed a sensitive peroxidase-antiperoxidase technique for the visualization of estrogen receptors in specimens, such as frozen tissue sections, through the use of a monoclonal antibody directed specifically against the receptors.

In the assay, two samples from the same specimen were placed on separate microscope slides prepared substantially in accordance with the procedure described in Example 1, above. The tissue-mount slides were processed through the fixative steps soon after preparation but were not allowed to air dry. The samples were fixed in formalin, methanol and acetone. The samples were then treated with normal goat serum in phosphate buffer as a blocking agent to inhibit the non-specific binding of subsequent reagents. One of the samples was incubated with a primary antibody, i.e., an IgG fraction of a rat monoconal anti-estrogen receptor antibody (>0.1 μg/mL in phosphate buffer). The other sample was incubated with a control antibody, i.e., a normal IgG rat antibody (>0.1 μg/mL in phosphate buffer). The purpose of the control antibody was to evaluate nonspecific binding of the reagents to the sample. The slides were then incubated with a bridging antibody (an ancillary specific binding member), i.e., goat anti-rat antibody (>0.1 μg/mL in phosphate buffer). The bridging antibody bound to the rat antibody against human estrogen receptor in the sample treated with the primary antibody, and bound to the normal rat IgG which had bound to the sample treated with control antibody. A labeled antibody, i.e., a conjugate of horseradish peroxidase and rat anti-peroxidase antibody (>0.1 μg/mL in Tris buffer), was contacted to each sample. The conjugate bound to the anti-rat IgG bridging antibody. A chromagen substrate solution of hydrogen peroxide and diaminobenzidine ·4 HCI (DAB) was then added to each sample. The reaction of peroxidase with hydrogen peroxide converted the DAB to an insoluble reddish-brown product. The estrogen receptor-monoclonal antibody complexes could then be visualized with a light microscope. Assay validity was determined by staining a positive control sample, such as a frozen section of breast cancer tissue, cells from a human breast cancer cell line or calf uterine tissue known to be estrogen receptor positive.

Example 3

Whole Cell Mount

Slides were prepared by placing a drop of a suspension of tissue culture cells, in tissue culture medium, upon hexadimethrine bromide precoated slides. The slides were then incubated in a humidity chamber for 10 to 30 minutes at room temperature. After incubation, the excess media was removed from the slide, and the slide was processed through the following fixative steps:

1) the slides were placed in 3.7% formaldehyde-PBS for 10 to 15 minutes or in Zamboni's fixative for approximately 20 minutes.
2) the slides were transferred to a PBS bath for four to six minutes.
3) the slides were transferred to a cold methanol bath at −10° to −25° C. for three to five minutes; then transferred to cold acetone at −10° to −25° C. for one to three minutes.
4) the slides were transferred to fresh PBS and rinsed for four to six minutes.

The slides were then ready to be used in an immunocytochemistry assay or stored in a specimen storage medium for future use. Drop slides prepared from tissue culture cells rich in estrogen receptor and assayed with the Abbott ER-ICA Monoclonal resulted in the nuclei of estrogen receptor-rich cells being stained brown by the immunocytochemical reaction. Estrogen receptor-poor cell nuclei were stained blue/light-purple with a weak hematoxylin counterstain and lacked the brown stain. Staining was quantified by estimating or counting the percent of cells containing the brown reaction product of the immunocytochemical staining procedure. The role of hexadimethrine bromide was to enhance attachment of the tissue culture cells to the slide such that the cells remained upon the slide during the fixation and staining process.

Example 4

Smear Slides

Smear slides were prepared to simulate fine-needle aspirates. A large number of tissue culture cells were removed from a cell culture bottle with a spatula and smeared onto hexadimethrine bromide precoated slides which were prepared substantially in accordance with the procedure described in Example 1, above. The smear slides were immediately processed through the fixative steps as described in Example 3, above.

Smear slides prepared from tissue culture cells rich in estrogen receptor and assayed with Abbott ER-ICA Monoclonal resulted in nuclei of estrogen receptor-rich cells being stained brown by the immunocytochemical reaction. Estrogen receptor-poor cell nuclei were stained blue/light-purple with a weak hematoxylin counterstain and lacked the brown stain. Staining was quantified by estimating or counting the percent of cells containing the brown reaction product of the immunocytochemical staining procedure. The role of hexadimethrine bromide was to enhance attachment of the tissue culture cells to the slide such that the cells remained upon the slide during the fixation and staining process.

Example 5

Comparative Reagent Testing

Tissue mounts, drop slides and smear slides which are prepared with uncoated slides often result in a loss of tissue sections or cells from the solid support during immunocytochemical processing. Poly-1-lysine has been used to enhance cell adhesion, but poor cell attachment and loss of tissue sections during the fixative and assay steps was still a significant problem. A variety of materials were evaluated by determining whether the material attained greater adhesion of tissue sections or cells than that achieved with poly-1-lysine, whether the material affected immunocytochemical staining, and whether slides could be precoated significantly in advance of their use or whether they needed to be freshly coated.

Various quaternary ammonia compounds were tested to determine which would be equivalent to or better than poly-1-lysine for use as a tissue or cell adhesive. The following reagents were tested at concentrations of 0.01% (w/v) and 1.0% (w/v). Celquat L-200, Celquat H-100, GAF Copolymer 845, Merquat 100 and hexadimethrine bromide.

Each of the reagents was prepared in distilled or deionized water at the listed concentrations and was coated onto microscope slides using either an overnight coating or a five minute coating. No wash step was used after coating the solid support. The poly-1-lysine control was coated with 0.01% (w/v) poly-1-lysine for five minutes and was then washed two times in distilled or deionized water. The different test slides were compared with the poly-1-lysine control slides using a drop cell method of preparation of tissue culture cells containing human estrogen or progesterone receptor. The slides were fixed and visually evaluated for cell attachment via a light microscope.

Upon visual evaluation, the GAF Copolymer 845 reagent failed to produced any slides (0 of 16 slides) which demonstrated cell attachment. Celquat H-100 had a few cells attached with the 1.0% (w/v) coating for five minutes (¾ slides), but no slides (0/12 slides) showed cell attachment at other concentrations. Celquat L-200 had a few slides with cells attached (7/16 slides). In each instance, the coating was observed to be peeling from the slide.

The Merquat 100 and hexadimethrine bromide reagents produced solid supports which had cells attached on every slide (16/16 slides). These slides were then processed for estrogen receptor immunocytochemical assays as described above. The Merquat 100 slides exhibited spotty attachment and some large areas with no cells attached to the deposition area. Conversely, the cells on the hexadimethrine bromide precoated slides exhibited superior cell attachment with greater uniformity over the deposition area in comparison with the Merquat 100 slides. The poly-1-lysine, Merquat 100 and hexadimethrine bromide precoated slides exhibited equivalent staining at the 0.01% (w/v) concentration or each. Thus, while the reagents appeared similar in their noninterference with assay reagents, only the hexadimethrine bromide adhesive compositions provided the maximum amount of sample adhesion with enhanced uniformity of sample adhesion throughout the deposition area.

Example 6

Comparative Hexadimethrine Bromide Composition Testing

A study was performed comparing poly-1-lysine coated slides to hexadimethrine bromide precoated slides which were prepared from hexadimethrine bromide compositions of varying concentrations. A solution of poly-1-lysine was prepared in distilled or deionized water at a final concentration of 0.01% (w/v). The poly-1-lysine microscope slides were submerged in the coating solution for five minutes and rinsed twice in distilled or deionized water for one minute. The hexadimethrine bromide precoated slides were coated overnight and dried at 37° C. using final concentrations ranging from about 0.003% (w/v) to about 0.3% (w/v) in deionized or distilled water. Table 1 illustrates the cell adhesion results of hexadimethrine bromide by recording that percentage of a microscopic field in which cells had adhered upon application to the precoated solid support.

TABLE 1

| Hexadimethrine bromide concentration (w/v) | Attachment |
|---|---|
| 0.003% | 40% of field |
| 0.01% | 50% of field |
| 0.03% | 40% of field |
| 0.06% | 40% of field |
| 0.1% | 10% of field |
| 0.3% | 40% of field |

In comparison, cells attached to only 30% of the viewed deposition area of poly-1-lysine coated slides. Thus, hexadimethrine bromide at all concentrations tested (except the 0.1% (w/v) concentration in this particular experimental trial) was more effective in producing uniform cell adhesion than was poly-1-lysine.

Example 7

Comparative Reagent Testing

Poly-1-lysine coated slides were compared to hexadimethrine bromide coated slides. The slides had been coated by incubation in the reagents for varying times from five minutes to one hour, with or without two distilled or deionized water rinses. All slides were air dried. Table 2 illustrates the comparative results of the hexadimethrine bromide compositions. Cell staining was considered "good" when the staining intensity was substantially equivalent to that found with poly-1-lysine in an immunocytochemical assay.

TABLE 2

| Time | Cell Attachment | | Cell Staining | |
|---|---|---|---|---|
| | With Rinse | No Rinse | With Rinse | No Rinse |
| 5 minutes | 50% field | 70% field | Good | Good |
| 15 minutes | 60% field | 60% field | Good | Good |
| 30 minutes | 70% field | 60% field | Good | Good |

TABLE 2-continued

| | Cell Attachment | | Cell Staining | |
|---|---|---|---|---|
| Time | With Rinse | No Rinse | With Rinse | No Rinse |
| 1 hour | 60% field | 70% field | Good | Good |

Each of the slides which did not undergo a rinse exhibited a bare spot at the center or bottom of the sample deposition area. The percentage of cell attachment on these slides was determined by evaluating a visual field exclusive of the bare spot.

In comparison, the poly-1-lysine control slides had only 20% of the field covered with cells, for each of the incubation periods. Hexadimethrine bromide compositions, however, resulted in better cell attachment than did poly-1-lysine, for each incubation time tested. In addition, cell attachment was higher when slides were prepared with a rinsing step. The slides were used in an immunocytochemical staining assay, and the assay was not interfered with by hexadimethrine bromide.

Example 8

Comparative Reagent Testing

Slides were coated with 0.01% (w/v) hexadimethrine bromide or 0.01% (w/v) poly-1-lysine for five minutes and were then rinsed two times in distilled or deionized water and air dried. Smears of human breast cancer cells, from a cultured cell line, were applied to the respective slides for cell attachment. These slides were then used in an estrogen receptor immunocytochemical assay. Both reagents resulted in slides which demonstrated "good" cell staining. The poly-1-lysine reagent, however, resulted in only a 20% of field cell attachment rating as compared to a 90% of field cell attachment rating achieved with the 0.01% (w/v) hexadimethrine bromide adhesive composition.

Example 9

Comparison of Cell Staining with Tissue Sections

Tissue sections from 17 human clinical specimens were evaluated using slides coated with 0.01% hexadimethrine bromide versus 0.01% (w/v) poly-1-lysine. For each tumor, one tissue section was applied to each of two hexadimethrine bromide coated slides and one tissue section was applied to each of two poly-1-lysine coated slides. The slides were then used in immunocytochemical staining assays substantially similar with the procedure described in Example 2, above.

There was no background staining with the control antibody on either the poly-1-lysine or hexadimethrine bromide slides. The primary antibody staining on each slide appeared equivalent when scored as "percent cells stained" by the immunocytochemical staining procedure. For example, percent cells stained in a progesterone immunocytochemical staining procedure, when compared by linear regression for hexadimethrine bromide coated slides plotted on the Y axis and poly-1-lysine coated slides on the X axis, for 15 tumor samples resulted in a correlation coefficient of 0.979, an intercept of −0.22 and a slope of 0.951. A similar comparison of 11 tumor samples for percent cells stained in an estrogen receptor assay resulted in a correlation coefficient of 0.999, an intercept of −0.13 and a slope of 0.989.

It will be appreciated by one skilled-in-the-art that many of the concepts of the present invention are equally applicable to other types of analytes, conjugates and solid support materials. The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:

1. A method for preparing histological samples for observation, comprising:
   a) applying a sample of tissue or cell to a microscope slide having at least one substantially dry sample deposition area formed from the evaporation of an adhesive composition, comprising a solution of about 0.003% (w/v) to about 1.0% (w/v) 1,5-dimethyl-1,5-diazaundecamethylene polymethobromide;
   b) allowing the sample to adhere to said microscope slide; and
   c) staining the sample.

2. The method of claim 1, further comprising the step of placing the microscope slide, with the adhered and stained sample, under a microscope for observation.

* * * * *

UNITED STATES PATENT AND TRADEMARK OFFICE
CERTIFICATE OF CORRECTION

PATENT NO. : 5,411,894
DATED : May 2, 1995
INVENTOR(S) : D. L. Cotter, B.L. Abry, R.A. Weigand It is certified that error appears in the above-indentified patent and that said Letters Patent is hereby corrected as shown below:

Column 10, line 5, change "or each" to -- of each --.

Signed and Sealed this

Twelfth Day of September, 1995

BRUCE LEHMAN

Attest:

*Attesting Officer*     *Commissioner of Patents and Trademarks*